(12) United States Patent
Torikata et al.

(10) Patent No.: US 10,197,960 B2
(45) Date of Patent: Feb. 5, 2019

(54) IMAGE FORMING APPARATUS INCLUDING IMAGE PROJECTOR

(71) Applicant: CANON KABUSHIKI KAISHA, Tokyo (JP)

(72) Inventors: Kotaro Torikata, Chigasaki (JP); Dai Kanai, Abiko (JP); Teppei Nagata, Abiko (JP); Hideki Mori, Toride (JP); Makoto Matsuo, Kashiwa (JP); Jun Shirayanagi, Ushiku (JP); Kenta Koyama, Tokyo (JP); Hideki Takaoka, Kawasaki (JP); Masatoshi Lin, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/825,567

(22) Filed: Nov. 29, 2017

(65) Prior Publication Data

US 2018/0157201 A1    Jun. 7, 2018

(30) Foreign Application Priority Data

Dec. 5, 2016  (JP) ................................ 2016-236259

(51) Int. Cl.
*G03G 15/00* (2006.01)
*G03F 1/84* (2012.01)
(Continued)

(52) U.S. Cl.
CPC ..... *G03G 15/5016* (2013.01); *G01N 21/8806* (2013.01); *G03F 1/84* (2013.01);
(Continued)

(58) Field of Classification Search
USPC ........................ 399/9, 16, 18, 38, 42, 75, 81
See application file for complete search history.

(56) References Cited

U.S. PATENT DOCUMENTS

| 4,636,062 A | * | 1/1987 | Ohno | ................. G03B 27/6228 355/43 |
| 8,777,472 B2 | * | 7/2014 | Okada | ................ G03G 15/5016 362/551 |

FOREIGN PATENT DOCUMENTS

| JP | 07-049533 A | 2/1995 |
| JP | 2008-048011 A | 2/2008 |

(Continued)

OTHER PUBLICATIONS

U.S. Appl. No. 15/825,609, Kanzuhiro Watanabe Kenta Koyama Hideki Takaoka Masatoshi Lin Wataru Kaku, filed Nov. 29, 2017.

(Continued)

*Primary Examiner* — Hoan Tran
(74) *Attorney, Agent, or Firm* — Venable LLP

(57) ABSTRACT

An image forming apparatus includes a main assembly, a first openable portion provided on a first side of the main assembly, a second openable portion provided on a second side of the main assembly, a single projector portion, a first projecting portion configured to project the image from above the first openable portion onto a projection object provided on the first side or onto the first openable portion when the first openable portion is open, and a second projecting portion configured to project the image from above the second openable portion onto a projection object provided on the second side or onto the second openable portion when the second openable portion is open.

17 Claims, 11 Drawing Sheets

(51) Int. Cl.
*G01N 21/88* (2006.01)
*G03G 21/16* (2006.01)

(52) U.S. Cl.
CPC ..... *G03G 21/1604* (2013.01); *G03G 21/1633* (2013.01); *G03G 15/6502* (2013.01)

(56) References Cited

FOREIGN PATENT DOCUMENTS

| | | |
|---|---|---|
| JP | 2010-128120 A | 6/2010 |
| JP | 2017-069858 A | 4/2017 |

OTHER PUBLICATIONS

U.S. Appl. No. 15/825,632, Hideki Mori Jun Shirayanagi Dai Kanai Teppei Nagata Kotaro Torikata Makoto Matsuo Kenta Koyama Hideki Takaoka Masatoshi Lin, filed Nov. 29, 2017.

* cited by examiner (a)

(b)

IMAGE FORMING APPARATUS INCLUDING IMAGE PROJECTOR

FIELD OF THE INVENTION AND RELATED ART

The present invention relates to an image forming apparatus for displaying operation guidance for notifying an operator of an operation procedure such as clearance of paper jam or exchange of consumables.

Conventionally, in the image forming apparatus, such as a copying machine, of an electrophotographic type, in some cases, there is a need for an operator to perform operations such as the clearance of paper jam (jamming), the exchange of the consumables and parts, supply of a developer, supply of sheets, and the like. For that reason, in the image forming apparatus, on a screen of an operating portion, operation guidance for notifying the operator of pieces of information on an operation procedure, a state of the image forming apparatus and matters to be attended to has been displayed.

However, in some cases, an operator does not readily recognize an operation procedure and an operation position due to a small screen provided at an operating portion and a remoteness of the operation position from the screen of the operating portion.

Therefore, Japanese Laid-Open Patent Application (JP-A) 2010-128120 proposes that an image forming apparatus is provided with a plurality of screens and operation guidance is projected from a projector onto either of the screens depending on the operation position.

In the image forming apparatus disclosed in JP-A 2010-128120, operation contents are displayed on the screen by the projector. However, in order to cause the operator to intuitively recognize the operation guidance, it is desirable that the following operation guidance is displayed by projection from the projector. For example, a grip of a door to be operated or a grip portion of a unit to be pulled out is illuminated with light, or at a position close to an operation object, an arrow indicating an operation direction or an image or motion pictures explaining an operation method is displayed.

As regards the image forming apparatus, in consideration of an operation from a front side where an operating portion is provided, exchange of consumables and setting of sheets from the front side are enabled. Further, in some cases, in the image forming apparatus, clearance of paper jam and manual setting of the sheets from a side surface (for example, a right (side) surface as seen from the front side) different from the front side are enabled.

Accordingly, an image forming apparatus capable of projecting operation guidance onto projection objects, provided at different side surfaces, by a single projector has been desired.

SUMMARY OF THE INVENTION

A principal object of the present invention is to provide an image forming apparatus capable of properly projecting operation guidance onto projection objects, provided at different side surfaces, by a single projector.

According to an aspect of the present invention, there is provided an image forming apparatus comprising: a main assembly including an image forming portion configured to form an image on a recording material; a first openable portion provided on a first side of the main assembly and capable of being pulled out from the first side or being rotated relative to the first side; a second openable portion provided on a second side of the main assembly and capable of being pulled out from the second side or being rotated relative to the second side; a single projector portion configured to project an image; a first projecting portion configured to project the image from the projector portion, from above the first openable portion onto a projection object provided on the first side or onto the first openable portion when the first openable portion is open; and a second projecting portion configured to project the image from the projector portion, from above the second openable portion onto a projection object provided on the second side or onto the second openable portion when the second openable portion is open.

Further features of the present invention will become apparent from the following description of exemplary embodiments with reference to the attached drawings.

Figure 3:
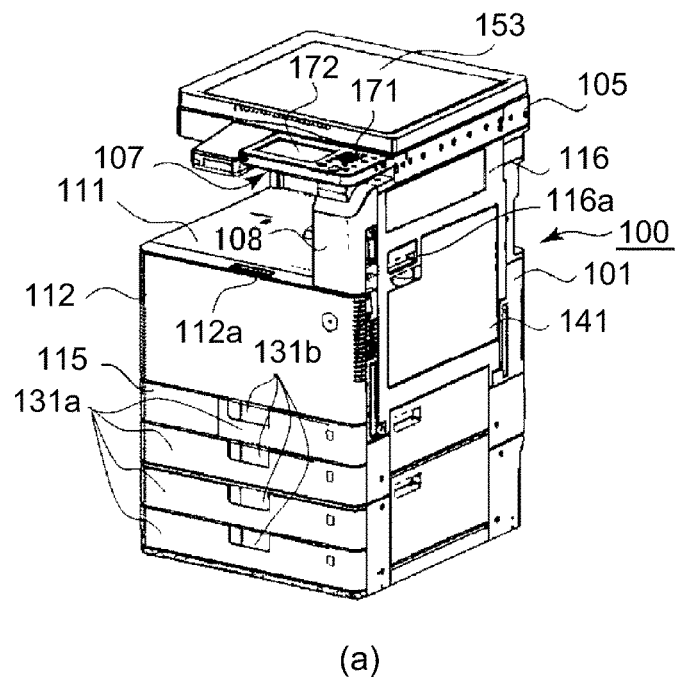
Figure 3:
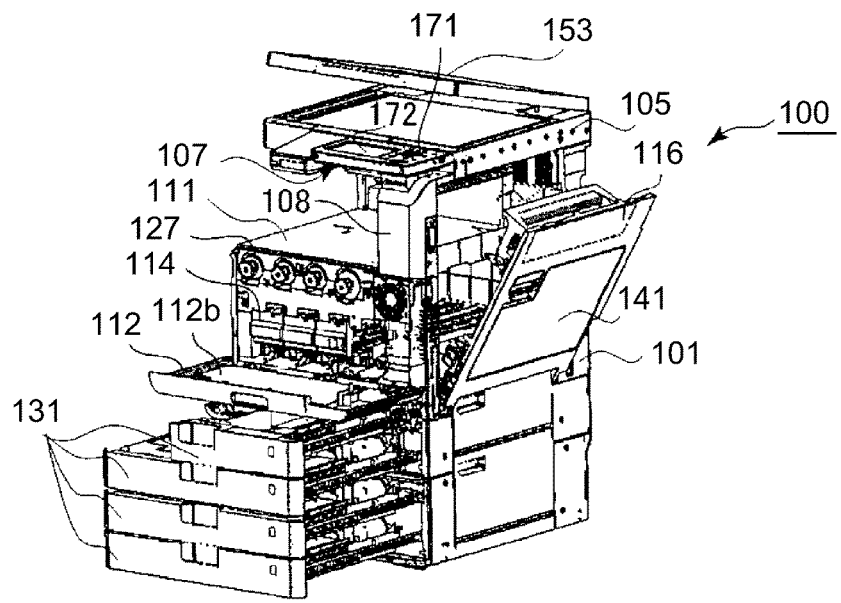

Parts (a) and (b) of FIG. 3 are perspective views of the image forming apparatus.

Figure 4:
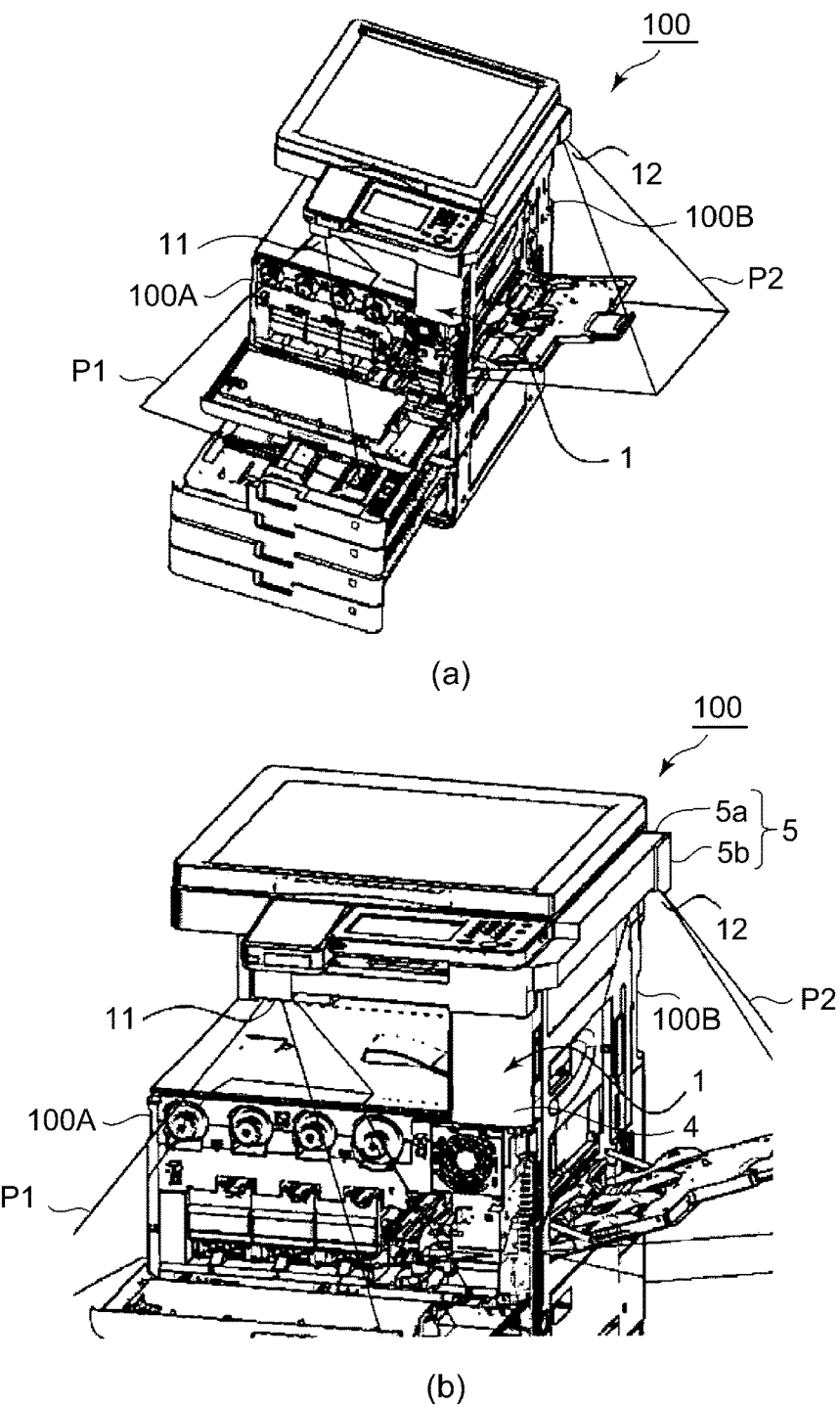

Parts (a) and (b) of FIG. 4 are perspective views of the image forming apparatus on which a projector unit is mounted.

Figure 5:
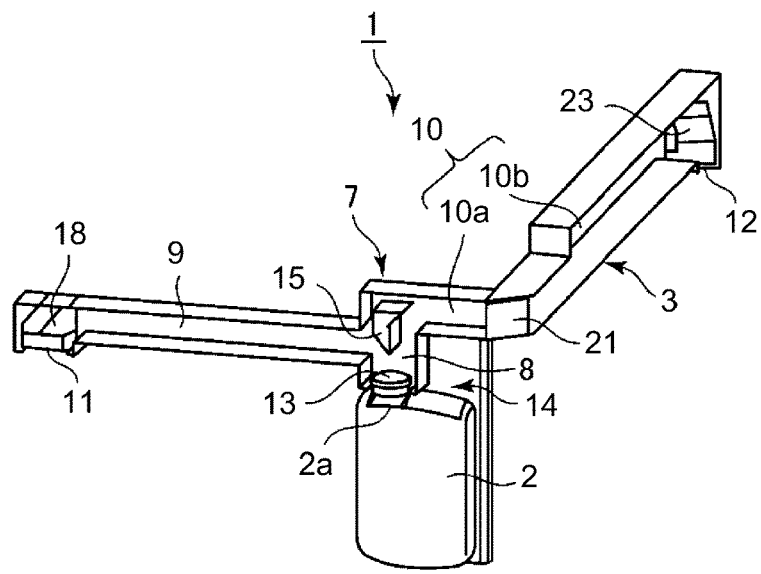

FIG. 5 is a perspective view showing the projector unit in a state in which an outside cover is removed.

Figure 6:
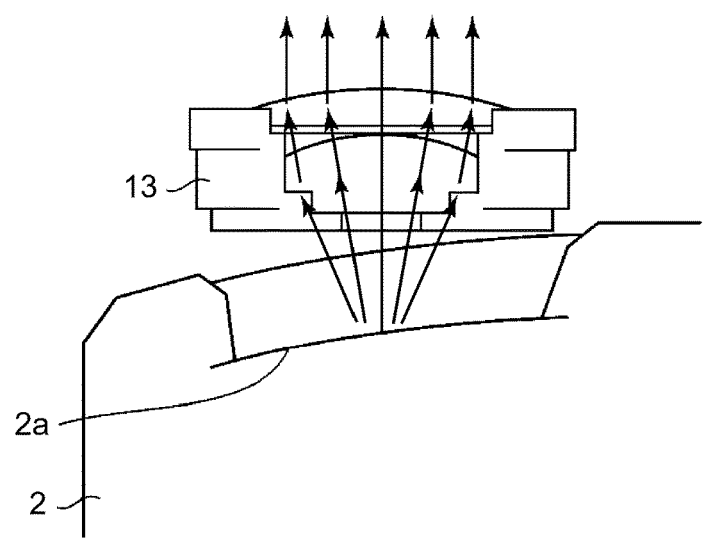

FIG. 6 is a front view of the projector unit in the neighborhood of a lens unit.

Figure 7:
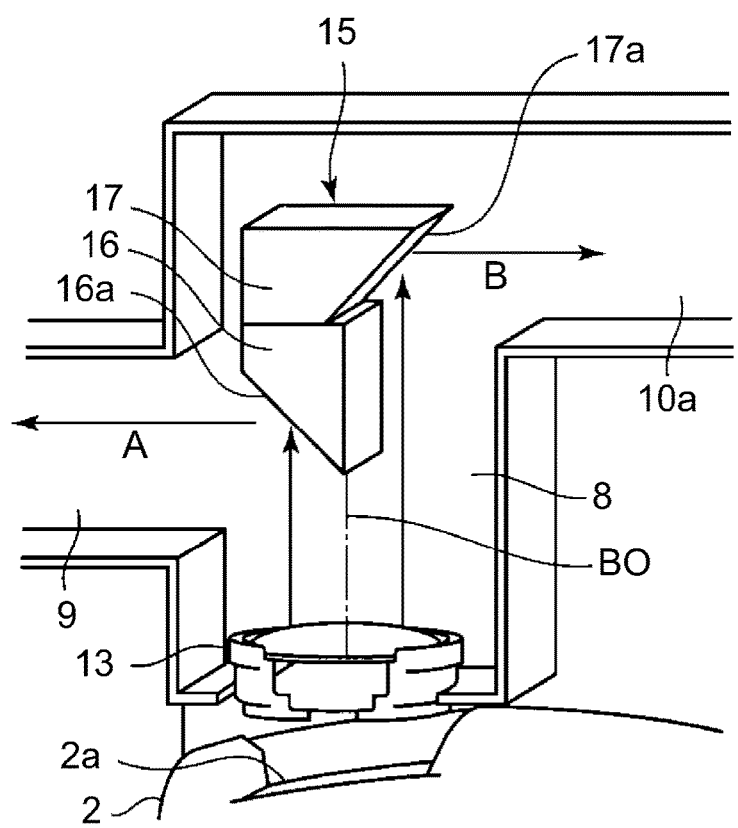

FIG. 7 is a perspective view of the projector unit in the neighborhood of a distribution reflection unit.

Figure 8:
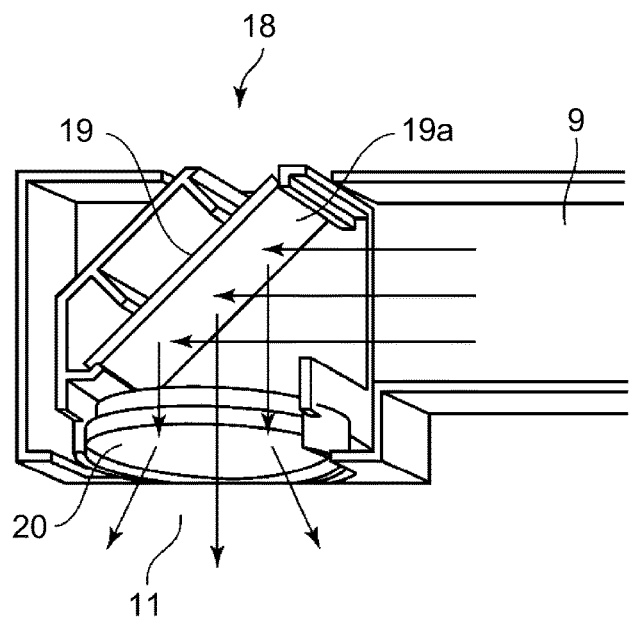

FIG. 8 is a perspective view of the projector unit in the neighborhood of a first projection unit.

Figure 9:
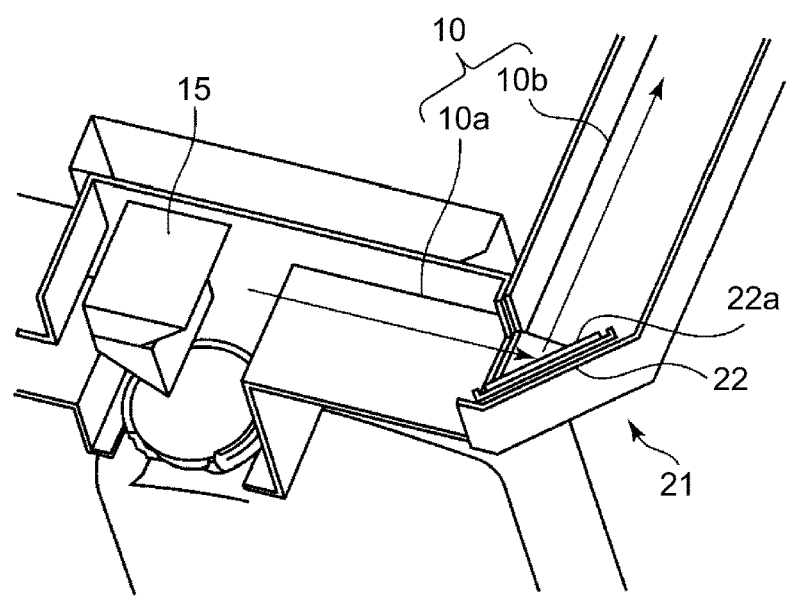

FIG. 9 is a perspective view of the projector unit in the neighborhood of a deflection reflection unit.

Figure 10:
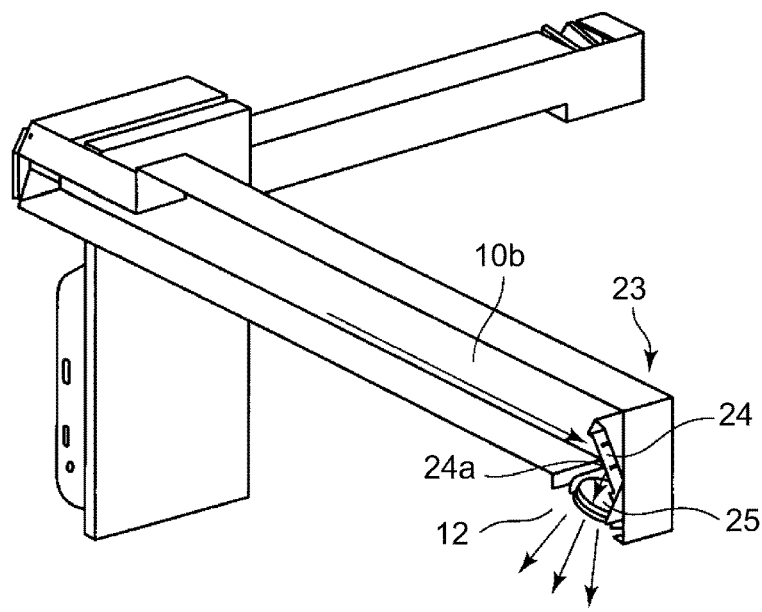

FIG. 10 is a perspective view of the projector unit in the neighborhood of a second projection unit.

Figure 11:
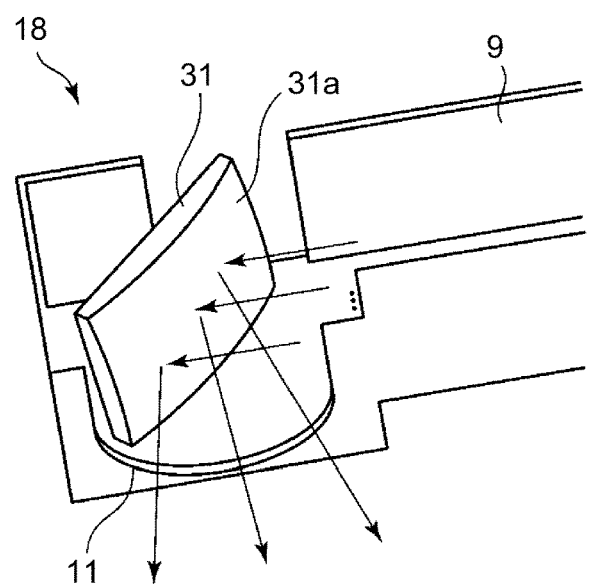

FIG. 11 is a perspective view of the projector unit for illustrating a modified example of the first projection unit.

Figure 12:
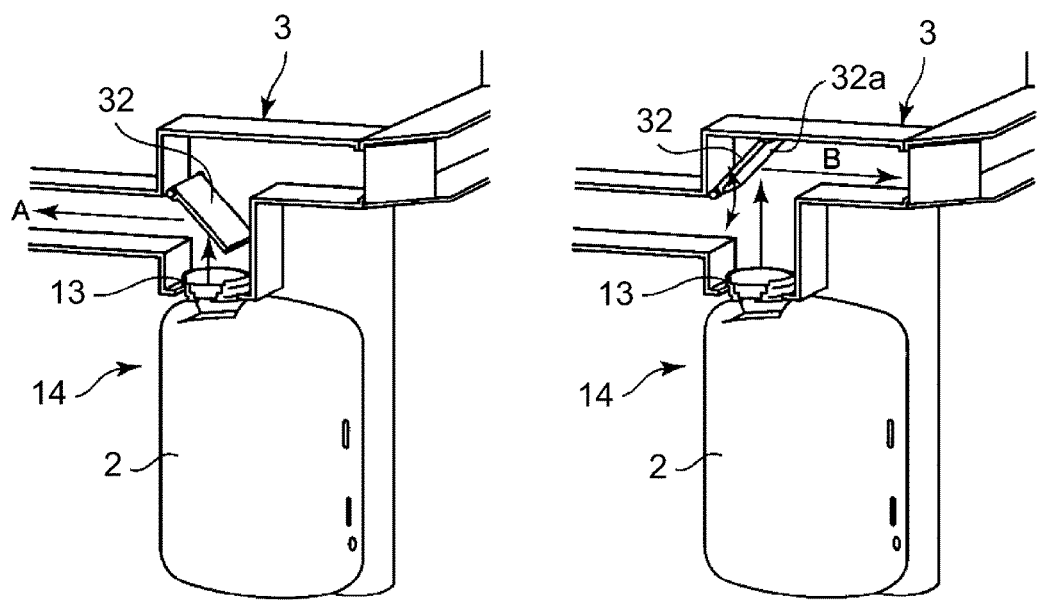
Figure 12:
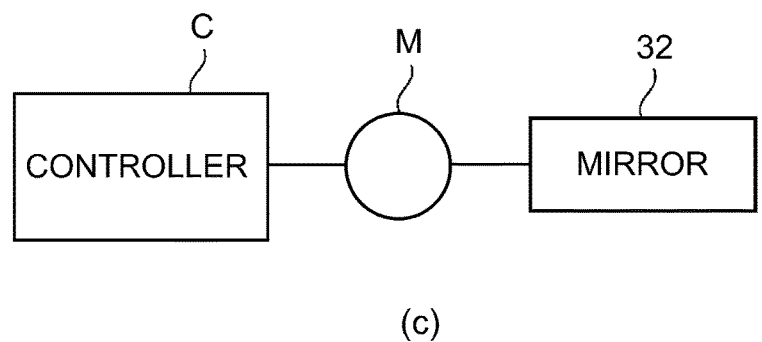

Parts (a) and (b) of FIG. 12 are perspective views for illustrating a modified example of a distributing portion and part (c) of FIG. 12 is a block diagram for illustrating the modified example of the distributing portion.

Figure 13:
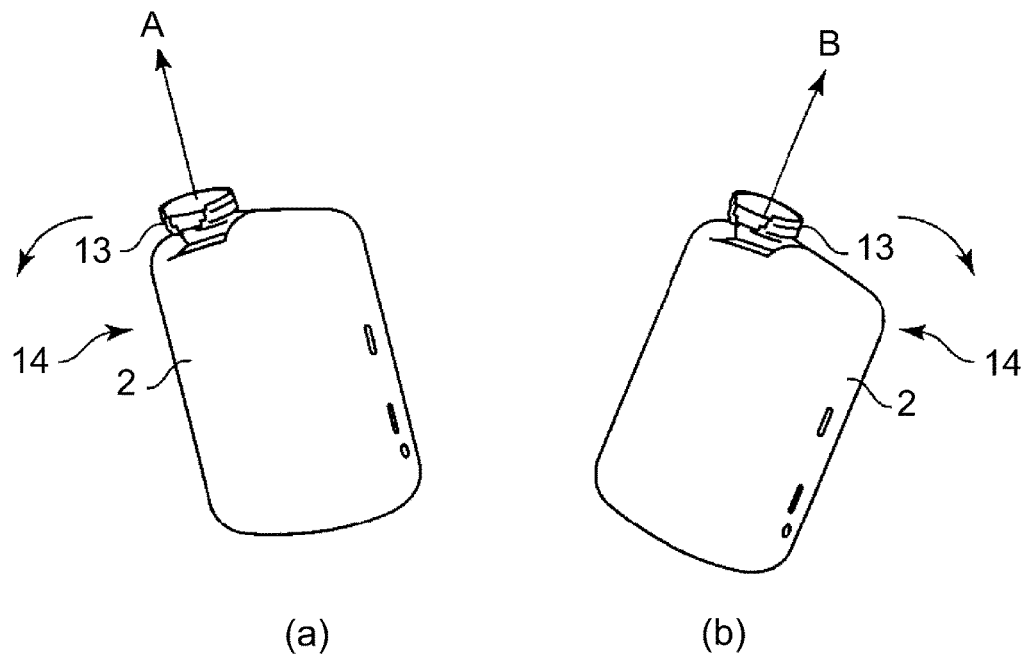
Figure 13:
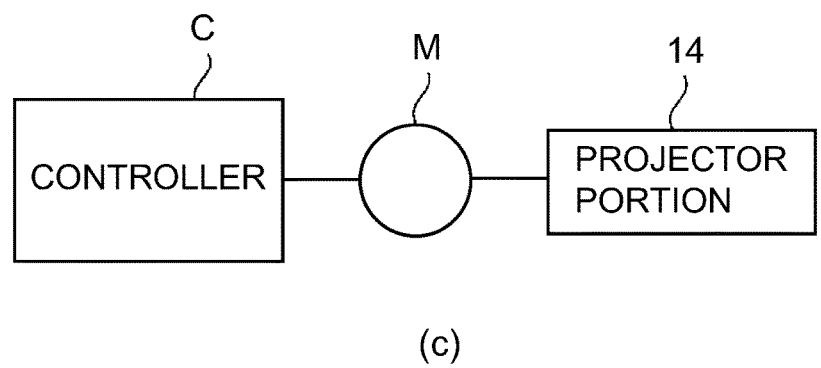

Parts (a) and (b) of FIG. 13 are schematic views for illustrating another modified example of the distributing portion, and part (c) of FIG. 13 is a block diagram for illustrating the modified example of the distributing portion.

Figure 14:
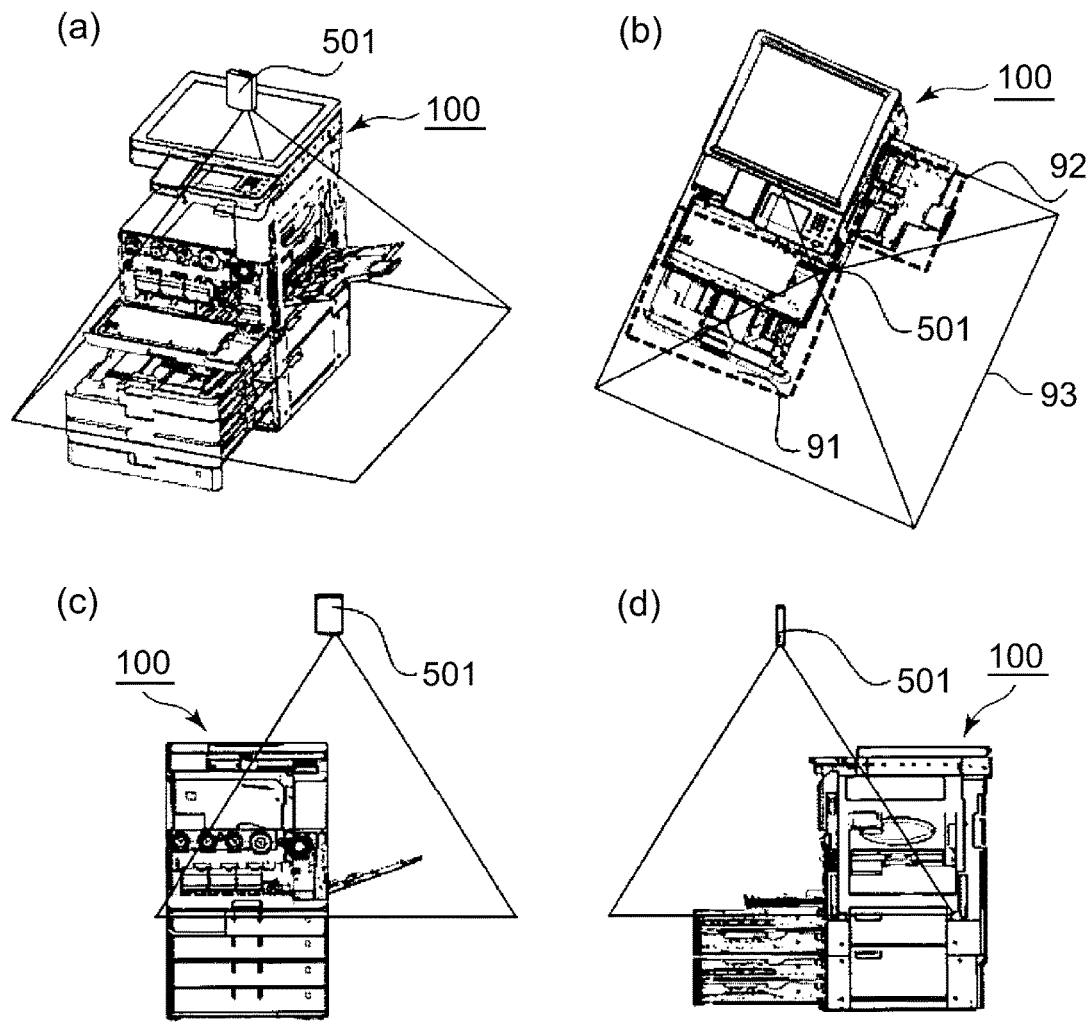

Parts (a) to (d) of FIG. 14 are schematic views for illustrating an example of a constitution for projecting operation guidance from above the image forming apparatus onto projection objects on a front side and a right surface of the image forming apparatus by a single projector.

DESCRIPTION OF EMBODIMENTS

An image forming apparatus according to the present invention will be specifically described with reference to the drawings.

Embodiment 1

1. General Structure of Image Forming Apparatus

Figure 1:
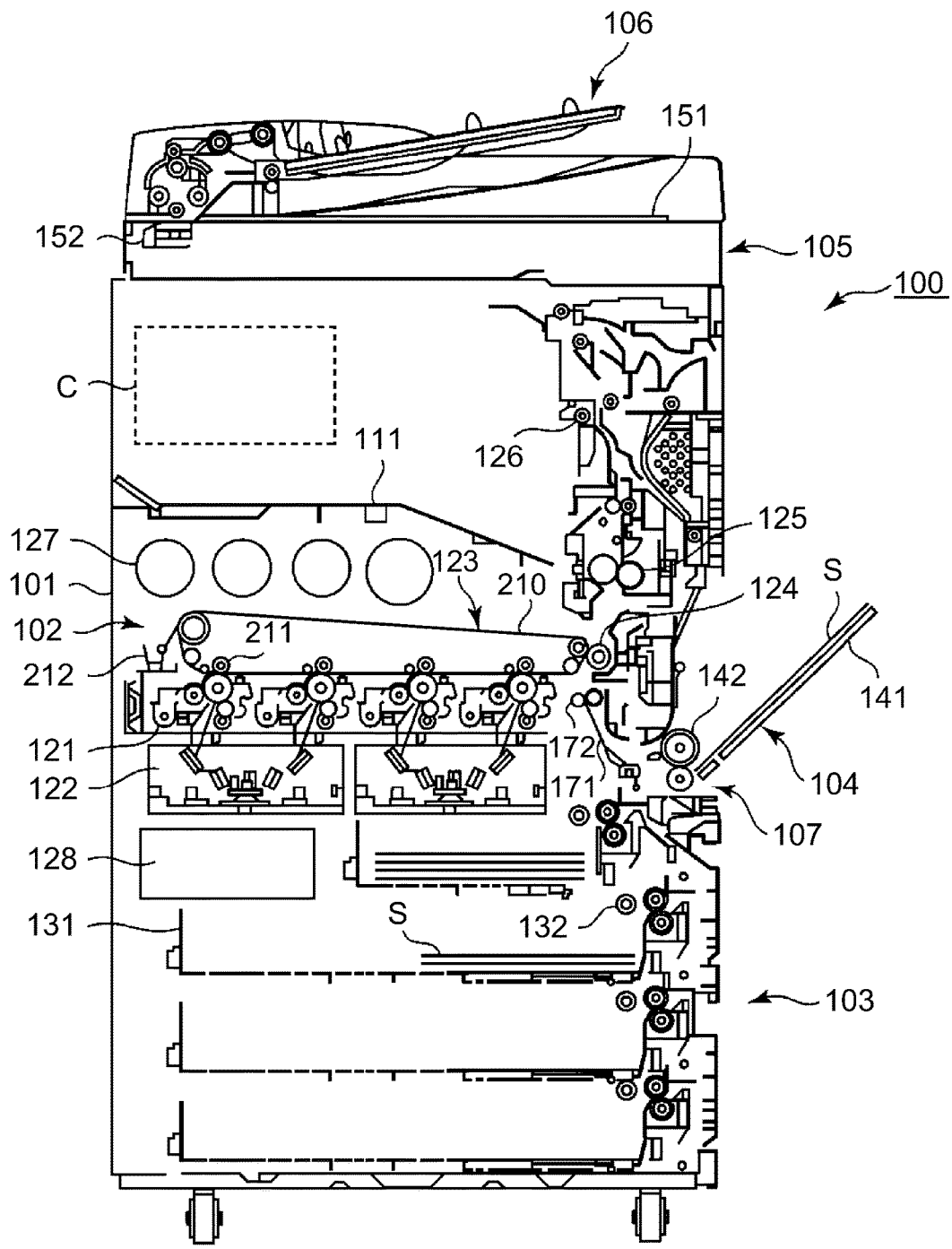
FIG. 1 is a sectional view of an image forming apparatus in Embodiment 1.

FIG. 1 is a sectional view of an image forming apparatus 100 in this embodiment. The image forming apparatus 100 in this embodiment is a multi-function machine which is capable of forming a full-color image by using an electrophotographic type and which has functions of a copying machine, a printer and a facsimile machine.

Here, as regards the image forming apparatus 100, a front side of the surface of the drawing sheet of FIG. 1 is a "front surface (or front)", and a rear side of the surface of the drawing sheet of FIG. 1 is a "rear (surface) (or back (surface))". A depth direction (front-rear direction) connecting the front side and the rear side of the image forming apparatus 100 is substantially parallel to a rotational axis direction of a photosensitive drum 203 (described later). Further, a left-right direction as to the image forming apparatus 100 is a left-right direction in the case where the image forming apparatus 100 is seen from the front side. Further, an up-down direction as to the image forming apparatus 100 refers to an up-down direction, but does not mean only just above and just below, and includes an upper side and a lower side with respect to a horizontal plane passing through a noted element or position. These directions refer to directions in a state in which the image forming apparatus 100 is installed so that the image forming apparatus 100 can be normally used.

The image forming apparatus 100 includes an apparatus main assembly 101. In the apparatus main assembly 101, an image forming portion 102, a sheet feeding device 103, a manual feeding portion 104, an original reading portion 105, a sheet feeding (conveying) portion 107, a controller C and the like are provided.

Figure 2:
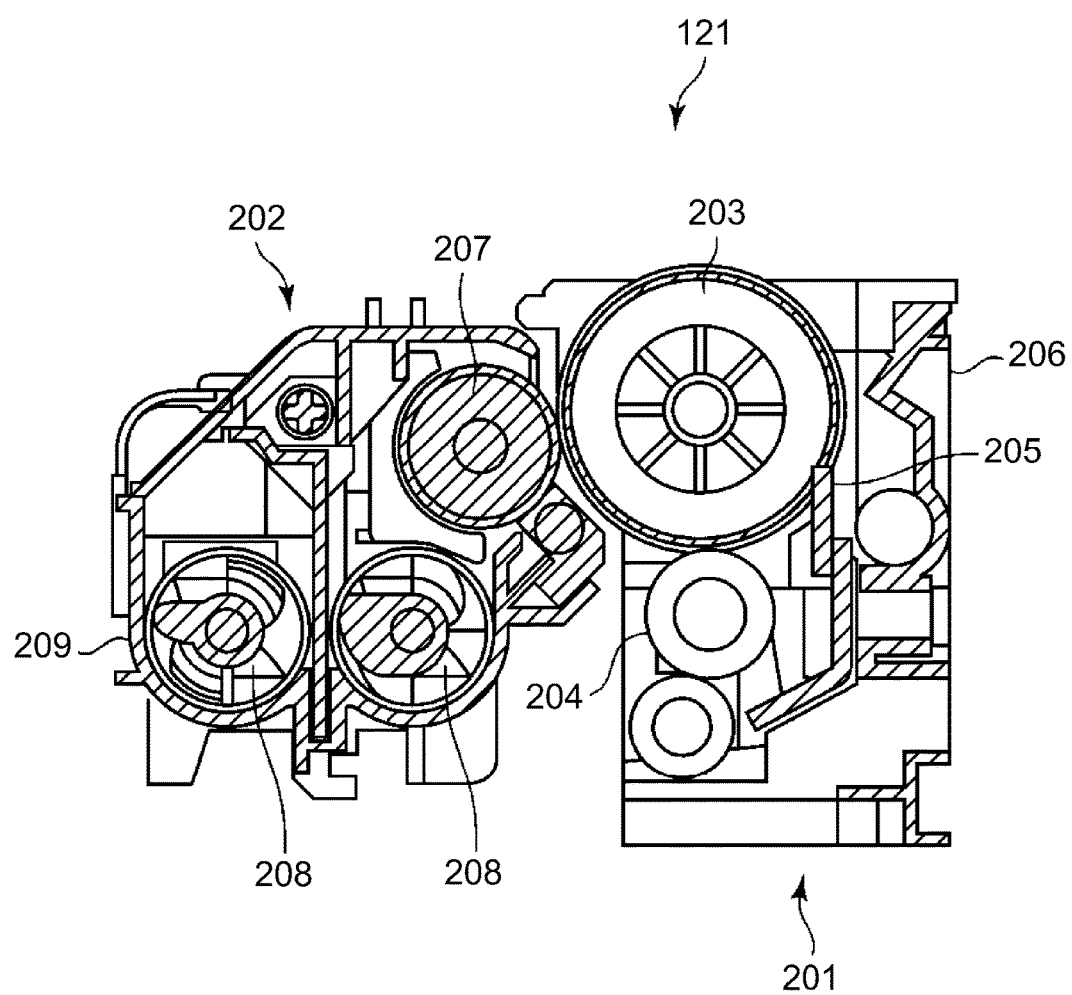
FIG. 2 is a sectional view of a process unit.

The image forming portion 102 includes a process unit 121, a laser scanner unit 122, an intermediary transfer unit 123, a secondary transfer roller 124, a fixing device 125, a discharging roller 126, a toner cartridge 127, a collecting container 128 and the like. In this embodiment, four process units 121 are provided and arranged substantially in a horizontal direction. These four process units 121 have substantially the same constitution except that colors of toners used for image formation are different from each other. FIG. 2 is a sectional view specifically showing a single process unit 121 as being representative.

The process unit 121 includes a drum unit 201 and a developing unit 202. The drum unit 201 is constituted by a photosensitive drum 203 which is a drum-shaped (cylindrical) photosensitive member (electrophotographic photosensitive member), a charging roller 204, a drum cleaner 205, and a drum unit container 206 for supporting these members. The developing unit 202 is constituted by a developing roller 207, a feeding screw 208, and a developing unit container 209 for supporting these members and accommodating a developer. In this embodiment, the developing unit 202 uses, as the developer, a two-component developer containing toner (non-magnetic toner particles) and a carrier (magnetic carrier particles). The drum unit 201 and the developing unit 202 are individually detachably mountable to the apparatus main assembly 101 by being inserted into and pulled out from the apparatus main assembly 101. The intermediary transfer unit 123 is constituted by an intermediary transfer belt 210 stretched by a plurality of stretching rollers, primary transfer rollers 211 provided in an inner peripheral surface side of the intermediary transfer belt 210 so as to be disposed correspondingly to the respective photosensitive drums 203, and a belt cleaner 212 and the like. In this embodiment, correspondingly to the four predetermined units 121, four toner cartridges 127 are provided and arranged substantially in the horizontal direction. In the toner cartridges 127, toners of yellow (Y), magenta (M), cyan (C) and black (K) are accommodated, respectively. The respective toner cartridges 127 are individually detachably mountable to the apparatus main assembly 101 by being inserted into and pulled out from the apparatus main assembly 101.

The sheet feeding device 103 is constituted by a plurality of sheet accommodating portions 131 as accommodating members for accommodating sheets (transfer materials, recording materials) S such as recording sheets, a feeding roller 132 for feeding the sheets S accommodated in the sheet accommodating portion 131, and the like. The sheet accommodating portion 131 is capable of being pulled out toward the front side of the apparatus main assembly 101.

The manual feeding portion 104 is constituted by a manual feeding tray 141 on which the sheets S are stacked, a manual feeding roller 142 for feeding (sending) the sheet(s) S stacked on the manual feeding tray 141, and the like. The manual feeding tray 141 is provided on a right-hand side surface of the apparatus main assembly 101 so as to be openable. In the case where the manual feeding portion 104 is used, the manual feeding tray 141 is opened and projected to a position where the sheets S are feedable, and the sheets S are stacked on the projected manual feeding tray 141.

The original reading portion 105 is constituted by a platen glass 151 as an original carriage, a reading device 152, and the like. The reading device 152 optically reads an original stacked (put) on the platen glass 151 and converts the read data into an electric signal. In FIG. 1, in order to permit continuous reading of a plurality of originals by the reading device 152, at an upper portion of the original reading portion 105, an automatic original (document) feeding device 106 is provided. In FIGS. 3 and 4, a state in which in place of the automatic original feeding device 106, a pressure plate 153 for pressing the original put on the platen glass 151 is mounted is shown.

The sheet feeding portion 107 is constituted by the surface feeding device 103, a sheet feeding path 171 along which the sheet S is sent from the manual feeding portion 104, a registration roller pair 172 for carrying out correction of oblique movement of the sheet S and control of feeding timing of the sheet S, and the like.

The collecting container 128 is a container for collecting the toner discharged as waste from the image forming portion 102. The collecting container 128 is detachably mountable to the apparatus main assembly 101 by being inserted into and pulled out from the apparatus main assembly 101.

In this embodiment, operations of the respective portions of the image forming apparatus 100 are subjected to centralized control by the controller C provided in the apparatus main assembly 101.

2. Image Forming Operation

An image forming operation of the image forming apparatus 100 will be described by taking a copying operation as an example. When an image reading signal is outputted from the controller C to the image reading portion 105, an image of the original is read by the image reading portion 105, and image information is sent to the image forming portion 102. In the image forming portion 102, the surface of the photosensitive drum 203 electrically charged uniformly by the charging roller 204 is irradiated with laser light corresponding to the image information from the laser scanner unit 122, so that an electrostatic latent image (electrostatic image) is formed on the photosensitive drum 203. The electrostatic latent image formed on the photosensitive drum 203 is developed (visualized) by being supplied with the toner by the developing unit 202, so that a toner image is formed on the photosensitive drum 203. The toner image formed on the photosensitive drum 203 is primary-transferred, at a primary transfer portion where the intermediary transfer belt 210 and the photosensitive drum 203 are in contact with each other, onto the intermediary transfer belt 210 by the action of the primary transfer roller 211. For example, during full-color image formation, the toner images of yellow, magenta, cyan and black are successively primary-transferred superposedly from the respective photosensitive drums 203 onto the intermediary transfer belt 210.

On the other hand, when a sheet feeding signal is outputted from the controller C to the sheet feeding device 103, the sheet S is fed from the sheet accommodating portion 131 by the feeding roller 132. When the sheet feeding signal is outputted from the controller C to the manual feeding portion 104, the sheet S is sent from the manual feeding tray 141 by the manual feeding roller 142. Thereafter, the sheet S is conveyed along the sheet feeding path 171, and not only the oblique movement of the sheet S is corrected by the registration roller pair 172 but also the sheet S is timed to the toner images on the intermediary transfer belt 210, and then the sheet S is sent to a secondary transfer portion where the intermediary transfer belt 210 and a secondary transfer roller 124 are in contact with each other.

At the secondary transfer portion, the toner images formed on the intermediary transfer belt 210 are secondary-transferred onto the sheet S by the action of the secondary transfer roller 124. The sheet S on which the toner images are secondary-transferred is heated and pressed by the fixing device 125, so that the toner images are fixed (melt-fixed) on the sheet S. The sheet S on which the toner images are fixed is discharged and stacked by the discharging roller 126 on a discharge tray 111 as a stacking portion provided at an outer portion of the apparatus main assembly 101.

Further, toner (primary transfer residual toner) remaining on the photosensitive drum 203 after a primary transfer step is removed and collected from the photosensitive drum 203 by the drum cleaner 205. Further, toner (secondary transfer residual toner) remaining on the intermediary transfer belt 210 after a secondary transfer step is removed and collected from the intermediary transfer belt 210 by a belt cleaner 212. The toners collected by the drum cleaner 205 and the belt cleaner 212 are accommodated in a collecting container 128 through a collecting toner feeding path (not shown). Further, the image forming portion 102 is provided with a toner hopper (not shown) in which the toner supplied from the toner cartridge 127 is stored and from which the toner in an amount corresponding to an amount of the toner consumed by the development is supplied to the developing unit 202. When the toner in the toner hopper is consumed by the development, the toner is supplied from the toner cartridge 127 to the toner hopper.

3. Operating Portion and the Like

Parts (a) and (b) of FIG. 3 are perspective views of the image forming apparatus 100 of which a front surface, a right side surface and an upper surface are shown, wherein part (a) of FIG. 3 shows a state in which an openable door member (described later) is closed and a pullable accommodating member is accommodated, and part (b) of FIG. 3 shows a state in which the openable door is open and the accommodating member is pulled out. Incidentally, in FIG. 3, within the image forming apparatus 100, a projector unit 1 (described later) is shown in an unmounted state. In this embodiment, in a state in which the openable front door 3 is closed and a pullable accommodating member is accommodated, in the case where the image forming apparatus 100 is seen from above, the image forming apparatus 100 has a substantially rectangular shape such that a front side surface and a rear side surface are substantially parallel to each other and that a left side surface and a right side surface are substantially parallel to each other.

In this embodiment, the image forming apparatus 100 includes, on the front side surface, particularly on the front side surface of the image reading portion 105, an operating portion 107 for permitting input of various settings such as a process condition of the sheet S, a start instruction of the image forming operation, and the like to the controller C. In this embodiment, the operating portion 107 is provided so as to project from the front side surface of the image reading portion 105 toward the front side. Further, in this embodiment, when the image forming apparatus 100 is seen from the front side, the operation portion 107 is provided in a right side more than a central portion with respect to a left-right direction.

The operating portion 107 is constituted by buttons (switches) 171 as input means for permitting input of instructions to the controller C, and a display (liquid crystal screen) 172 as a display means for displaying information for an operator such as a user or a maintenance person. In this embodiment, the display 172 is constituted by a touch panel and also has a function of an input means. The operator operates, in general, the operating portion 107 from the front side of the image forming apparatus 100, so that the operator can input necessary items to the controller C and can cause the image forming apparatus 100 to start the image forming operation.

Further, the image forming apparatus 100 is configured so that the operator can perform maintenance (exchange) from the front side of the image forming apparatus 100 where the operator portion 107, provided outside the image forming apparatus 100, for inputting an instruction regarding the operation of the image forming apparatus 100 is provided. That is, on the front side surface of the image forming apparatus 100, a front door 112 as a door member openable for exposing at least a part of the image forming portion 102 to the outside of the image forming apparatus 100 is provided. The front door 112 is connected with the apparatus main assembly 101 rotatably by a hinge provided at a lower-side end portion. By operation of a front door grip (recess-shaped portion) 112a, the front door 112 can be opened by being rotated from above toward below about a rotational axis substantially parallel to the horizontal direction and can be closed by being rotated from below toward above about the rotational axis (horizontal direction hinge).

When the front door 112 is opened, end portions of the toner cartridges 127 in the front side and small doors 114 for exposing end portions of the process units 121 in the front side to an outside of the image forming apparatus 100 are exposed to the outside of the image forming apparatus 100. In this embodiment, four toner cartridges 127 and four small doors 114 are provided and arranged substantially in the horizontal direction correspondingly to four process units 121. Each of the toner cartridges 127 can be mounted into and demounted from the apparatus main assembly 101 by being inserted into and pulled out from the apparatus main assembly 101 in the front-rear direction by operating a cartridge grip (portion) 127a provided at the end portion thereof in the front side. Further, by opening the small door 114, the drum unit 201 and the developing unit 202 can be mounted into and demounted from the apparatus main assembly 101 by being individually inserted into and pulled out from the apparatus main assembly 101 in the front-rear direction. The small door 114 is opened by being rotated from above toward below about a rotational axis substantially parallel to the horizontal direction, and is closed by being rotated from below toward above about the rotational axis. In this embodiment, the small door 8 also functions as a lever as a portion-to-be-operated for changing the state of the drum unit 201 and the developing unit 202 between a detachably mountable state and a set state.

In the front side of the image forming apparatus 100, accommodating portion outer surfaces 131a which form a front side surface of the sheet accommodating portion 131 are provided below the front door 112. In this embodiment, four accommodating portion outer surfaces 131a are disposed and arranged in an up-down direction, and a size of the uppermost accommodating portion outer surface 131a with respect to a left-right direction is smaller than a size of other accommodating portion outer surfaces 131a with respect to the left-right direction. The sheet accommodating portions 131 can be pulled out from and accommodated in the apparatus main assembly 101 by being pulled out and inserted along a front-rear direction through an operation of accommodating portion grips 131b provided on the accommodating portion outer surfaces 131a. In the sheet accommodating portion 131, in a state in which the sheet accommodating portion 131 is pulled out from the apparatus main assembly 101, the sheets S are set (accommodated).

Further, on the front side of the image forming apparatus 100, a collecting door 115 as a door member openable for exposing the collecting container 128 to an outside of the image forming apparatus 100 is provided below the front door 112. The collecting door 115 can be opened by being rotated from above toward below about a rotational axis substantially parallel to the horizontal direction and can be closed by being rotated from below toward above about the rotational axis. By opening the collecting door 115, the collecting container 128 can be mounted into and demounted from the apparatus main assembly 101 by being inserted into and pulled out from the apparatus main assembly 101.

Further, at an upper portion of the image reading portion 105, a pressure plate 153 (or an automatic document feeder 106 (FIG. 1) having a function of pressing the original (document)) for pressing the original put on a platen glass 151 when the image on the original is read is provided. The pressure plate 153 (or the automatic document feeder 106) is connected with the apparatus main assembly 101 rotatably by a hinge provided at a rear end portion. Further, the original can be put on the platen glass 151 by being opened in the upward direction about a rotational axis substantially parallel to the horizontal direction.

On the other hand, on the right side of the image forming apparatus 100, a right(-hand) door 116 openable for clearance of a jam (i.e., removal of the jammed sheet S) in a sheet feeding path 171 is provided. The right door 116 is connected rotatably with the apparatus main assembly 101 by a hinge provided at a lower end portion thereof. The right door 116 is opened by operation a right door grip 116a so as to be rotated from above toward below about a rotational axis substantially parallel to the horizontal direction. By opening the right door 116, the sheet S positioned in the sheet feeding path 171 can be removed. The right door 116 is provided with a manual feeding portion 104. The manual feeding tray 141 of the manual feeding portion 104 is connected rotatably with the right door 116 by the hinge provided at the lower end portion of the right door 116. As regards the manual feeding tray 141, by operation a manual feeding tray grip 141a, the manual feeding tray 141 can be opened by being rotated from above toward below about the rotational axis substantially parallel to the horizontal direction and can be closed by being rotated from below toward above about the rotational axis. On the manual feeding tray 141, in an open state, the sheets S are set (mounted).

In the front side, a cylindrical surface 108 between the operating portion 107 and the front door 112 with respect to the up-down direction is a fixed surface which is not operated by an opening and closing operation. Further, at the right side surface of the image forming apparatus 100, the right side surface of the image reading portion 105 and a side surface to the rear of the right door 116 are fixed surfaces which are not operated by the opening and closing operation.

4. Problem in Case where Operation Guidance is Projected onto a Plurality of Side Surfaces by Single Projector A problem in the case where the operation guidance is projected from above onto the projection objects disposed on two (side surface) sides, adjacent to each other, of the image forming apparatus by the single projector will be described further. Parts (a) to (d) of FIG. 14 are schematic views for illustrating one constitution assumed in that case.

In order to project the operation guidance from above onto the projection objects on the front side and the right side by a single projector 501, as shown in FIG. 14, it would be considered that the projector 501 is provided at a position protruded from the image forming apparatus 100 toward the upper side, the front side and the right side. This is because projection regions (91 and 92 in part (b) of FIG. 14) including the projection objects on both of the front side and the right side are ensured.

In the case of such a constitution, also a supporting member for supporting the projector 501 on the image forming apparatus 100 is protruded together with the projector 501. For that reason, when the operator intends to perform an operation, there is a liability that the supporting member constitutes an obstacle to the operation. Further, in such a case, on the front side, the projection by the projector 501 is carried out so as to extend from the left side toward the right side, and therefore, in the case where the operation is carried out with a right hand of the operator, there is a liability that a shadow of the right hand generates on a projected image. Further, on the right side surface, the projection is carried out so as to extend from the front side toward the rear side, and therefore, in the case where the operator stands in front of the image forming apparatus 100 and performs the operation, there is a liability that the shadow by the hand of the operator generates on the projected image.

Further, in such a case, in order to ensure the projection regions (91 and 92 of part (b) of FIG. 14) including the projection objects on both of the front side and the right side, there is a need to prepare a large projectable region (93 of part (b) of FIG. 14) of the projector 501. For that reason, there is a liability that a pixel per unit area is roughened and an image or moving images (pictures) for the operation guidance become a roughened image which is difficult to understand.

5. Projector Unit

Next, a projecting means for projecting the operation guidance (guidance display, guiding display) will be described.

Part (a) of FIG. 4 is a perspective view showing the front side surface, the right side surface and the upper surface of the image forming apparatus 100 in which the projector unit 1 described below is mounted, and part (b) of FIG. 4 is a partially enlarged view of part (a) of FIG. 4. In FIG. 4, a state in which the front door 112 is open, the sheet accommodating portions 131 are pulled out, a part of the small doors 114 is open, and the manual feeding tray 141 is open is shown.

In this embodiment, as shown in FIG. 4, the projector unit 1 is mounted on the cylindrical surface 108 ((b) of FIG. 3) at the front side surface of the image forming apparatus 100, at the lower portion of the operating portion 107, and on the right side surface of the image reading portion 105 of the image forming apparatus 100. The projector unit 1 is capable of projecting the operation guidance from above onto each of the projection object disposed on a front side surface (first side surface) 100A side of the image forming apparatus 100 and the projection object disposed on a right side surface (second side surface) 100B side of the image forming apparatus 100. In part (a) of FIGS. 4, P1 and P2 are projectable regions including the front side projection object and the right side projection object, respectively, of the image forming apparatus 100. The projector unit 1 includes a projector cover 4 accommodating therein a projector 2 (described later), and a lens-barrel (tube body) casing 5 (a lens-barrel casing body 5a and a lens-barrel cover 5b) accommodating elements of a lens-barrel unit 3 (described later) and constituting a part of the lens-barrel unit 3.

Incidentally, the projection from above is not limited to projection from above toward below with respect to a vertical direction, but may also include projection toward below with an angle with respect to the vertical direction. For example, as regards the projectable region P1 on the front side, the following can be said. That is, in the case where the image forming apparatus 100 is seen from the front side, the projection may be carried out from upper left toward lower right and from upper right toward lower left, and in the case where the image forming apparatus 100 is seen from the right side, the projection can be carried out from above on the rear side toward below on the front side and from above on the front side toward below on the rear side. This is also true for the right side projectable region P2. In this embodiment, as regards the front side projectable region, a projection optical axis (optical axis of a projection image to be projected through a first projection opening 11 (described later)) of the projector unit 1 extends downward with respect to a substantially vertical direction. Here, "extends downward with respect to a substantially vertical direction" includes not only the case where the optical axis extends downward with respect to a completely vertical direction but also the case where the optical axis is deviated from the downward direction with respect to the vertical direction within an approximate error range (for example, about ±10 degrees). Further, as regards the right side projectable region P2, the projection optical axis (optical axis of a projection image to be projected through a second projection opening 12 (described later)) of the projector unit 1 is inclined with respect to the vertical direction so as to extend from above on the rear side toward below on the front side when the image forming apparatus 100 is seen from the right side. Further, the operation guidance may also be in any form such as illumination, characters, symbols, figures (diagrams), still images (pictures) or moving images (animation), for instructing or illustrating an operating portion, an operating direction, an operating method or the like.

FIG. 5 is a perspective view showing the projector unit 1 in a state in which the projector cover 4 and the lens-barrel cover 5b (FIG. 4) constituting an outside surface of the lens-barrel casing 5 are removed. The projector unit 1 is constituted by the projector 2 and a lens-barrel unit 3 including a lens through which a light beam for forming an image projected from the projector 2 passes and including a mirror.

In this embodiment, the projector 2 is constituted so as to be also usable as a projection device alone. The projector 2 is disposed on the cylindrical surface 108 on the front side surface of the image forming apparatus 100. The projector 2 is supported by the apparatus main assembly 101 or the lens-barrel casing 5. The projector 2 is disposed so as to project the image upward. That is, the projector 2 is disposed so that a projection opening 2a thereof faces upward (toward the operating portion 107 side).

The lens-barrel unit 3 includes a lens-barrel portion 7 through which the light beam projected from the projector 2 passes. The lens-barrel portion 7 is formed by the lens-barrel casing 5. The lens-barrel portion 7 includes a first lens-barrel portion 8 extending in the up-down direction substantially parallel to an optical axis direction (projection direction) of the projector 2. Further, the lens-barrel portion 7 includes a second lens-barrel portion 9 separated from the first lens-barrel portion 8 and extending in the leftward direction substantially parallel to the horizontal direction and includes a third lens-barrel portion 10 separated from the first lens-barrel portion 8 and extending in the rightward direction substantially parallel to the horizontal direction.

That is, the first lens-barrel portion extending upward, i.e., toward a downstream side with respect to an optical axis direction, is separated into two directions substantially parallel to the optical axis direction. The second lens-barrel portion 9 as one of the two lens-barrel portions extending in the two directions extends in the leftward direction substantially parallel to the front side surface of the image forming apparatus 100 on the lower side of the operating portion 107, i.e., extends toward a substantially central portion of the image forming apparatus 100 with respect to the left-right direction. Thus, the first and second lens-barrel portions 8 and 9 are disposed on the front side surface of the image forming apparatus 100. Further, the third lens-barrel portion 10 as the other one of the two lens-barrel portions extending in the two directions extends in the rightward direction substantially parallel to the front side surface of the image forming apparatus 100 on the lower side of the operating portion 107, i.e., extends toward the right side surface of the image forming apparatus 100. Further, the third lens-barrel portion 10 is folded at substantially right angles, along a corner portion formed by the front side surface and the right side surface of the image forming apparatus 100, toward the rear side of the image forming apparatus 100 and extends toward the rear side along the right side surface of the image reading portion 105. Thus, the third lens-barrel portion 10 is constituted by a first portion 10a provided on the front side surface of the image forming apparatus 100 and a second portion 10b provided on the right side surface of the image forming apparatus 100.

At a free end portion (left side end portion) of the second lens-barrel portion 9, the first projection opening 11 for permitting projection of an image from above onto the projection object disposed on the front side of the image forming apparatus 100 is formed. Further, at a free end portion (rear side end portion) of the second portion 10b of the third lens-barrel portion 10, a second projection opening 12 for permitting projection of an image from above onto the projection object disposed on the right side of the image forming apparatus 100 is formed.

6. Lens-Barrel Unit

The lens-barrel unit 3 will be further described specifically. In this embodiment, the image projected from the projector 2 is magnified (enlarged) with an increasing distance from the projector 2 along the optical axis direction. That is, a light beam, projected from the projector, for forming the image has an angle toward a diverging direction from an optical axis center. For that reason, the lens-barrel unit 3 includes a lens unit 13 as a collimating portion as described below. The lens unit 13 changes the image, projected from the projector 2, to an image which is not magnified (or reduced) irrespective of a distance from the lens unit 13. That is, the lens unit 13 refracts the light beam forming the image from a state in which the angle diverges from the optical axis center to a state in which the light beam is substantially parallel to the optical axis.

FIG. 6 is a front view of the lens-barrel unit 3 in the neighborhood of the lens unit 13. The lens unit 13 can be constituted by a single lens or a plurality of lenses. In this embodiment, the lens unit 13 is constituted by including two convex lenses. The lens unit 13 is supported by the lens-barrel casing 5 so as to approach a projection opening 2a of the projector 2 at an upstream end portion of the first lens-barrel portion 8 with respect to the optical axis direction. By providing the lens unit 13, there is no need to magnify the lens-barrel portion, the mirror or the lens correspondingly to magnification of the image depending on the distance from the projector 2, so that downsizing of the projector unit 1 can be realized. In this embodiment, a projector portion 14 for projecting an image which is not magnified irrespective of the distance from the projector 14 is constituted by including the projector 2 and the lens unit 13.

Incidentally, "substantially parallel to the optical axis" may only require that the light beam is sufficiently parallel to the optical axis so as not to generate problematic image magnification (or reduction) in terms of an optical path length in the image forming apparatus, and therefore, includes not only the case where the light beam is completely parallel to the optical axis, but also the case where the light beam has an angle with respect to the optical axis within an approximate error range (for example, about ±10 degrees).

The lens-barrel unit 3 includes a distribution reflection unit 15, provided downstream of the lens unit 13 with respect to the optical axis direction, as a distributing portion for distributing the image, projected from the projector portion 14, to a first direction and a second direction. That is, the distribution reflection unit 15 distributes the image, projected from the projector 2, to the two directions consisting of the first direction passing through the second lens-barrel portion 9 and the second direction passing through the third lens-barrel portion 10. In this embodiment, the distribution reflection unit 15 reflects the light beam, passing through the lens unit 13 and extending toward above with respect to the substantially vertical direction, at right angles in the left-right direction.

FIG. 7 is a perspective view of the lens-barrel unit 3 in the neighborhood of the distribution reflection unit 15. The distribution reflection unit 15 includes a first distribution reflection member 16 and a second distribution reflection member 17. The first distribution reflection member 16 includes a first distribution reflection portion 16a which is a reflection surface for reflecting an image, of images projected from the projector 2, projected toward the first direction A onto the projection object disposed in the front side of the image forming apparatus 100. The second distribution reflection member 17 includes a second distribution reflection portion 17a which is a reflection surface for reflecting an image, of images projected from the projector 2, projected toward the second direction B onto the projection object disposed in the right side of the image forming apparatus 100. That is, the first distribution reflection portion 16a reflects one image, of the images projected from the projector 2, eliminated by a boundary surface BO in FIG. 7 so that the light beam passes through an inside of the second lens-barrel portion 9. Further, the second distribution reflection portion 17a reflects the other image, of the images projected from the projector 2, eliminated by a boundary surface BO in FIG. 7 so that the light beam passes through an inside of the third lens-barrel portion 10. The first and second distribution reflection members 16 and 17 are supported by the lens-barrel casing 5.

In this embodiment, each of the first and second distribution reflection members 16 and 17 is constituted by a prism. Each of the prisms has a surface formed with an angle of 45° with respect to the optical axis. On the surfaces of the prisms, the first and second distribution reflection portions 16a and 17a which are reflection surfaces are formed, respectively, by deposition of aluminum. However, the first and second distribution reflection portions 16a and 17a are not limited to the above-described constitution, but may also be prepared by forming the reflection surfaces on a member of glass, resins or metals, through the deposition of aluminum. In this embodiment, the first and second distribution reflection portions 16a and 17a are formed on the first and second distribution reflection members 16 and 17 which are separate members, but may also be formed on a single member so as to be integrally constituted.

The lens-barrel unit 3 includes, at a downstream end portion (left side end portion) of the second lens-barrel portion 9 with respect to the optical direction, a first projection unit 18 as a first projecting portion for projecting the image, distributed in the first direction by the distribution reflection unit 15, from above onto the projection object disposed on the front side. The first projection unit 18 is disposed at a substantially central portion on the front side surface of the image forming apparatus 100 with respect to the left-right direction. The first projection unit 18 reflects and magnifies the image reflected by the distribution reflection unit 15 toward the substantially central portion, with respect to the left-right direction, along the front side surface of the image forming apparatus 100, and then projects the image downward (in the substantially vertical direction) through the first projection opening 11.

FIG. 8 is a perspective view of the lens-barrel unit 3 in the neighborhood of the first projection unit 18. The first projection unit 18 includes a first planar mirror (flat surface mirror) 19 as a first reflection member. The first planar mirror 19 includes a first reflection portion (mirror surface) 19a which is a reflection surface for reflecting the image from the distribution reflection unit 15 toward the projection object disposed on the front side of the image forming apparatus 100, i.e., downward with respect to the substantially vertical direction in this embodiment. Further, the first projection unit 18 includes a first magnifying lens 20 as a first magnifying portion on a side downstream of the first planar mirror 19 with respect to the optical axis direction. The first magnifying lens 20 changes the image, reflected by the first planar mirror 19, to an image magnified with an increasing distance from the first magnifying lens 20. That is, the first magnifying lens 20 refracts the light beam, for forming the image, from a state substantially parallel to the optical axis to a state having a diverging angle from the optical axis center. In this embodiment, the first magnifying lens 20 is constituted by a concave lens. The image passes through the first magnifying lens 20 and is projected through the first projection opening 11 toward the projection object disposed on the front side of the image forming apparatus 100. The first planar mirror 19 and the first magnifying lens 20 are supported by the lens-barrel casing 5.

In this embodiment, the first projection unit 18 is constituted by the planar mirror and the lens (concave lens) for magnifying and projecting the image. However, the first projection unit 18 is not limited to such a constitution, but may also be constituted by including a reflection magnification member 31 as shown in FIG. 11. The reflection magnification member 31 includes a reflection magnification portion (mirror surface) 31a which is a reflection surface formed in a curved shape so as to provide a convex central portion. The reflection magnification portion 31a not only reflects the image from the distribution reflection unit 15 toward the projection object disposed on the front side of the image forming apparatus 100, i.e., downward with respect to the substantially vertical direction in this embodiment, but also changes the image to the image magnified with the increasing distance from the reflection magnification portion 31a. That is, the first reflection magnification portion 31a changes the light beam forming the image from a state substantially parallel to the optical axis to a state having a diverging angle from the optical axis center.

In this embodiment, the first reflection member 19 is constituted by a planar mirror having a reflection surface formed on a glass member. However, the first reflection member 19 is not limited to such a constitution, but may also be prepared by forming a reflection surface on, e.g., a member of resin or metal, through the deposition of aluminum. Similarly, also the reflection magnification member 31 as shown in FIG. 11 may also be prepared by forming a reflection surface on, e.g., a member of glass, resin or metal, through the deposition of aluminum.

The lens-barrel unit 3 includes a deflection reflection unit 21 at a connecting portion between a downstream end portion (right side end portion) of the first portion 10a of the third lens-barrel portion 10 with respect to the optical axis direction and an upstream end portion (front side end portion) of the second portion 10b of the third lens-barrel portion 10 with respect to the optical axis direction. The deflection reflection unit 21 reflects the image, reflected by the distribution reflection unit 15 toward the right side surface along the front side surface of the image forming apparatus 100, at substantially right angles toward the rear side of the image forming apparatus 100 along a corner portion formed by the front side surface and the right side surface of the image forming apparatus 100.

FIG. 9 is a perspective view of the lens-barrel unit 3 in the neighborhood of the deflection reflection unit 21. The deflection reflection unit 21 includes a deflection planar mirror 22 as a deflection reflection member. The deflection planar mirror 22 includes a deflection reflection portion (mirror surface) 22a which is a reflection surface for reflecting the image, distributed by the distribution reflection unit 15 in the second direction along the front side surface of the image forming apparatus 100, in a direction toward a second projection unit 23, described later, along the right side surface. The deflection planar mirror 22 is supported by the lens-barrel casing 5 so that a surface of the deflection reflection portion 22a has an angle of 45° with respect to the optical axis. The deflection reflection member 22 may also have the same constitution as the first planar member 19.

The lens-barrel unit 3 includes, at a downstream end portion (right side end portion) of the second portion 10b of the third lens-barrel portion 10 with respect to the optical direction, a second projection unit 23 as a second projecting portion for projecting the image, distributed in the second direction by the distribution reflection unit 15, from above onto the projection object disposed on the right side. The second projection unit 23 is disposed at a rear side end portion on the right side surface of the image forming apparatus 100. The second projection unit 23 reflects and magnifies the image reflected by the deflection reflection unit 21 toward the rear side, along the right side surface of the image forming apparatus 100, and then projects the image downward (from above on the rear side toward below on the front side) through the second projection opening 12.

FIG. 10 is a perspective view of the lens-barrel unit 3 in the neighborhood of the second projection unit 23. The second projection unit 23 has the same constitution as the first projection unit 18 and includes a second planar mirror (flat surface mirror) 24 as a second reflection member. The second planar mirror 24 includes a second reflection portion (mirror surface) 24a which is a reflection surface for reflecting the image from the distribution reflection unit 15 toward the projection object disposed on the right side of the image forming apparatus 100, i.e., downward from above on the rear side toward below on the front side. Further, the second projection unit 24 includes a second magnifying lens 25 as a second magnifying portion on a side downstream of the second planar mirror 24 with respect to the optical axis direction. The second magnifying lens 25 changes the image, reflected by the second planar mirror 24, to an image magnified with an increasing distance from the second magnifying lens 25. That is, the second magnifying lens 25 refracts the light beam, for forming the image, from a state substantially parallel to the optical axis to a state having a diverging angle from the optical axis center. In this embodiment, the second magnifying lens 25 is constituted by a concave lens. The image passes through the second magnifying lens 25 and is projected through the second projection opening 12 toward the projection object disposed on the front side of the image forming apparatus 100. The second planar mirror 24 and the second magnifying lens 25 are supported by the lens-barrel casing 5. The second planar mirror 24 may also have the same constitution as the first planar mirror 19. Further, similarly as the first projection unit 18, also as regards the second projection unit 23, a constitution in which the image is not only reflected but also magnified using the reflection magnification member 31 as shown in FIG. 11 can be employed.

As shown in (a) of FIG. 4, on the front side surface of the image forming apparatus 100, by the first projection unit 18, the image constituting the operation guidance is magnified so as to include an operation portion (position) to be guided. Similarly, also on the right side surface, by the second projection unit 23, the image constituting the operation guidance is magnified so as to include an operation portion to be guided. For example, on the front side, in the case where opening of the front door 112 is guided, light is projected onto the front door grip 112a. Further, in the case where exchange of consumables is guided, an operation procedure is displayed on an inside surface 112b of the opened front door 112 or light is projected onto the consumables exposed to the front side of the apparatus main assembly 101. Further, on the right side surface, in the case where opening of the right door 116 is guided, light is projected onto the right door grip 116a. In the case where a procedure of clearance of a paper jam is guided, guidance indicating the operation portion or the like is displayed on an inside surface of the opened right position 116 or on the sheet feeding portion 107. At this time, the image magnification is carried out on each of the front side and the right side of the image forming apparatus 100, and therefore, the projection region does not largely include an unnecessary area. For that reason, it is possible to suppress difficulty of discrimination of the operation guidance due to a roughened image pixel.

In this embodiment, in the front side of the image forming apparatus 100, the projection is not carried out from above on the right side toward below on the left side. In the right side of the image forming apparatus 100, the projection is not carried out from above on the front side toward below on the rear side. For that reason, on the front side of the image forming apparatus 100, in the case where the operator performs the operation with a right hand, a possibility of generation of a shadow of the right hand of the operator on the projected image is reduced. Further, on the right side of the image forming apparatus 100, in the case where the operator stands in front of the image forming apparatus 100 and performs the operation, a possibility of generation of a shadow of the hand of the operator on the projected image is reduced. In this embodiment, the first projection unit 18 is disposed at the substantially central portion with respect to the left-right direction on the front side of the image forming apparatus 100, but an effect similar to that described above is obtained when the first projection unit 18 is disposed at the substantially central portion or on a left side rather than the central portion with respect to the left-right direction as seen from the front side. In this embodiment, the second projection unit 23 is disposed at the rear side end portion, but an effect similar to that described above is obtained when the second projection unit 23 is disposed at the substantially central portion or on a rear side with respect to the depth direction as seen from the front side.

As the projection objects, including the above-described projection objects, for the operation guidance by the projector unit 1, the following objects can be cited as an example. The projection objects may include outer portions (the outside surfaces and the grips of the front door 112, the small doors 114, the collecting door 115, the right door 116, and the manual feeding tray 141) of the door members openable on one of side surfaces of the image forming apparatus; inner portions (the inside surfaces and the front door 112, the small doors 114, the collecting door 115, the right door 116, and the manual feeding tray 141 and screens provided on the inside surfaces) of the door members; outer portions (the outside surface and the grip of the sheet accommodating portion 131) of the accommodating member pullable in one side surface side of the image forming apparatus; an inner portion (of the sheet accommodating portion 131) of the accommodating member in a state of being pulled out; an accommodated member (the sheet S in the sheet accommodating portion 131) accommodated in the accommodating member in the state of being pulled out; consumables (the toner cartridges 127, the drum units 201, the developing units 202) detachably mountable to the image forming apparatus in a state in which the door members are open; a portion-to-be-operated (the small doors 114) operated for mounting and demounting the consumables in the state in which the door members are open; sheet feeding portions (the sheet feeding path, the feeding members and the like) in the state in which the door members are open; portions-to-be-operated (the levers, the knobs and the like for moving the sheet feeding path and for moving (rotating) the feeding member) operated for removing the sheet from the sheet feeding portion; sheets (the recording sheet causing the paper jam and the like) on the sheet feeding portion in the state in which the door members are open; and a floor surface on one of the side surface sides of the image forming apparatus. Incidentally, a single projection object or a plurality of projection objects may be independently one of the above-cited members (portions). In a preferred example, the image projected onto the projection object disposed on the first side surface side is the operation guidance regarding an operation object disposed on the first side surface side, and the image projected onto the projection object disposed on the second side surface side is the operation guidance regarding an operation object disposed on the second side surface side. As a result, the operation guidance regarding the operation object can be displayed in the neighborhood of the operation object.

In this embodiment, the image can be simultaneously projected on the front side and the right side of the image forming apparatus 100. However, the projection of the image on the front side of the image forming apparatus 100 and the projection of the image on the right side of the image forming apparatus 100 may also be carried out in a switching manner. In that case, in place of the distribution reflection unit 15 in this embodiment, a constitution of a distributing portion as shown in parts (a) to (c) of FIG. 12 can be used. In an example of FIG. 12, the lens-barrel unit 3 includes a rotatable mirror 32 as the distribution reflection member. The mirror 32 includes a distribution reflecting portion (mirror surface) 32a movable between a first position (part (a) of FIG. 12) where the image from the projector 2 is reflected toward the first direction A and a second position (part (b) of FIG. 12) where the image from the projector 2 is reflected toward the second direction B. In this case, as shown in part (c) of FIG. 12, depending on the operation guidance to be projected, the controller C controls a driving source M so as to rotate the mirror 32 through a drive transmission member (not shown). As a result, the image can be projected selectively on the front side and the right side of the image forming apparatus 100 in a switching manner.

Further, as shown in parts (a) to (c) of FIG. 13, the projector portion 14 may also be moved between a first position (part (a) of FIG. 13) in the case of projecting the image onto the projection object on the front side and a second position (part (b) of FIG. 13) in the case of projecting the image onto the projection object on the right side. The projector portion 14 can employ the constitution including the projector 2 and the lens unit 13 similarly as this embodiment. In this case, as shown in part (c) of FIG. 13, depending on the operation guidance to be projected, the controller C controls the driving source M so as to change the direction of the projector portion 14 through the drive transmission member (not shown), and thus changes the projection direction (optical axis direction). As a result, it is possible to selectively project the image on the front side and the right side of the image forming apparatus 100 in a switching manner. The image projected from the projector portion 14 may be projected directly onto the first and second projection portions 18 and 23 and may also be guided to the first and second projection portions 18 and 23 by reflecting portions (mirrors) appropriately provided. In this case, a distributing portion for distributing the image, projected from the projector portion 14, into the first and second directions is constituted by including the driving source M and the like as a moving means for moving the projector 2.

In this embodiment, the projector 2 is also configured to be used alone as a projection device by being demounted from the projector unit 1. However, as the projector 2, a portion obtained by removing the projection lens portion, for magnifying and projecting the image, from the projector 2 in this embodiment may also be used. That is, the projector unit 1 can employ a constitution including a projector projecting the image which is not magnified (or reduced) irrespective of a distance from the projector. In this case, the lens-barrel unit 3 is not required to be provided with the lens unit 13.

As described above, according to this embodiment, the projector unit 1 is disposed at (in) the side surface of the image forming apparatus 100. In this embodiment, the optical path along which the light beam forming the image projected from the projector portion 14 is not magnified with the increasing distance from the projector portion 14 along the optical axis direction. For that reason, the lens-barrel unit 3 can be constituted so as not to largely protrude from the side surface of the image forming apparatus 100. In this embodiment, on the front side of the image forming apparatus 100, the image is projected from above toward below substantially at the central portion with respect to the left-right direction, and therefore, in the case where the operator performs the operation with the right hand, the possibility of the generation of the shadow of the right hand on the projected image can be reduced. Further, in this embodiment, on the right side of the image forming apparatus 100, the image is projected from above on the front side toward below on the rear side and therefore in the case where the operator stands in front of the image forming apparatus 100 and performs the operation, a possibility of generation of a shadow of the hand of the operator on the projected image can be reduced. In this embodiment, on each of the front side and the right side, the image magnification is carried out correspondingly to a necessary projection region including the projection objects, and therefore, it is possible to suppress that the projected image or the projected moving images are not readily in sight due to a roughened pixel per unit area. Accordingly, according to this embodiment, in the constitution in which the operation guidance is projected onto the projection objects on different side surface sides by the single projector, it is possible to suppress that the constitution as to the projection constitutes the obstacle to the operation, so that easy-to-understand operation guidance can be displayed.

Other Embodiments

As described above, the present invention was explained based on the specific embodiment, but the present invention is not limited to the above-described embodiment.

In the above-described embodiment, the projector portion was disposed on the front side surface of the image forming apparatus, but may also be disposed on the right side surface of the image forming apparatus, for example. In this case, it is only required that not only also the distributing portion is disposed on the right side surface but also the second lens-barrel portion through which the image distributed in the first direction is constituted by the first portion on the front side surface and the second portion on the right side surface and the third lens-barrel portion through which the image distributed in the second direction is disposed on the right side surface.

In the above-described embodiment, the projection means was the projection means projecting the image on the front side and the right side of the image forming apparatus, but the side surfaces, of the image forming apparatus, where the projection means projects the image are not limited to those on the front side and the right side. For example, the image may also be projected on the front side and the left side of the image forming apparatus. Further, for example, to the constitution of the above-described embodiment, a reflecting portion for reflecting the image, distributed in the second direction, toward the left side along the rear side surface on the rear side of the image forming apparatus or the like portion is added, so that the image may also be projected on the rear side of the image forming apparatus.

In the above-described embodiments, the present invention was applied to the color image forming apparatus, including the plurality of the image forming portions, but is also applicable to an image forming apparatus for a single color (for example, black), in which a single image forming portion is provided, so that it is possible to obtain effects similar to those in the above-described embodiment.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-236259 filed on Dec. 5, 2016, which is hereby incorporated by reference herein in its entirety.

What is claimed is:

1. An image forming apparatus comprising:
   a main assembly including an image forming portion configured to form an image on a recording material;
   a first openable portion provided on a first side of said main assembly and capable of being pulled out from the first side or being rotated relative to the first side;
   a second openable portion provided on a second side of said main assembly and capable of being pulled out from the second side or being rotated relative to the second side;
   a single projector portion configured to project an image;
   a first projecting portion configured to project the image from said projector portion, from above said openable portion onto a projection object provided on the first side or onto said first openable portion when said first openable portion is open; and
   a second projecting portion configured to project the image from said projector portion, from above said second openable portion onto a projection object provided on the second side or onto said second openable portion when said second openable portion is open.

2. An image forming apparatus according to claim 1, wherein said projector portion includes a projector configured to project the image and a collimator lens configured to collimate the image projected from said projector portion.

3. An image forming apparatus according to claim 1, wherein said first projecting portion includes a first projection opening through which the image is projected and includes a first pipe portion provided on the first side and configured to guide the image, projected from said projector portion, to said first projection opening, and
   wherein said second projecting portion includes a second projection opening through which the image is projected and includes a second pipe portion provided on the second side and configured to guide the image, projected from said projector portion, to said second projection opening.

4. An image forming apparatus according to claim 3, further comprising a distributing portion configured to distribute the image, projected from said projector portion, to said first pipe portion or said second pipe portion.

5. An image forming apparatus according to claim 4, wherein said distributing portion is a reflecting portion configured to reflect the image toward said first pipe portion or said second pipe portion.

6. An image forming apparatus according to claim 4, wherein said distributing portion is a switching portion configured to switch a direction of a projector of said projector portion toward said first pipe portion or said second pipe portion.

7. An image forming apparatus according to claim 4, wherein said distributing portion includes a prism configured to reflect the image toward said first pipe portion and a prism configured to reflect the image toward said second pipe portion.

8. An image forming apparatus according to claim 3, wherein each of said first projection opening and said second projection opening is provided with a magnifying lens configured to magnify the image.

9. An image forming apparatus according to claim 1, wherein the first side is a front side of said main assembly, and the second side is a side adjacent to the front side.

10. An image forming apparatus according to claim 9, further comprising an operating portion configured to operate said image forming apparatus,
wherein said operating portion is mounted on the front side.

11. An image forming apparatus according to claim 9, wherein said first openable portion is a front cover.

12. An image forming apparatus according to claim 9, wherein said first openable portion is a cassette configured to stack the recording material.

13. An image forming apparatus according to claim 9, wherein said second openable portion is a tray configured to stack thereon the recording material to be fed to said image forming portion.

14. An image forming apparatus according to claim 9, wherein said second openable portion is an openable cover configured to expose a feeding path along which the recording material is to be fed.

15. An image forming apparatus according to claim 9, wherein the projection object provided on the first side is an exchangeable image forming unit or an exchangeable toner bottle accommodating toner.

16. An image forming apparatus according to claim 9, wherein the projection object provided on the second side is a feeding path along which the recording material is to be fed.

17. An image forming apparatus according to claim 1, wherein said projector portion is provided between said first projecting portion and said second projecting portion.

* * * * *